Figure 1:
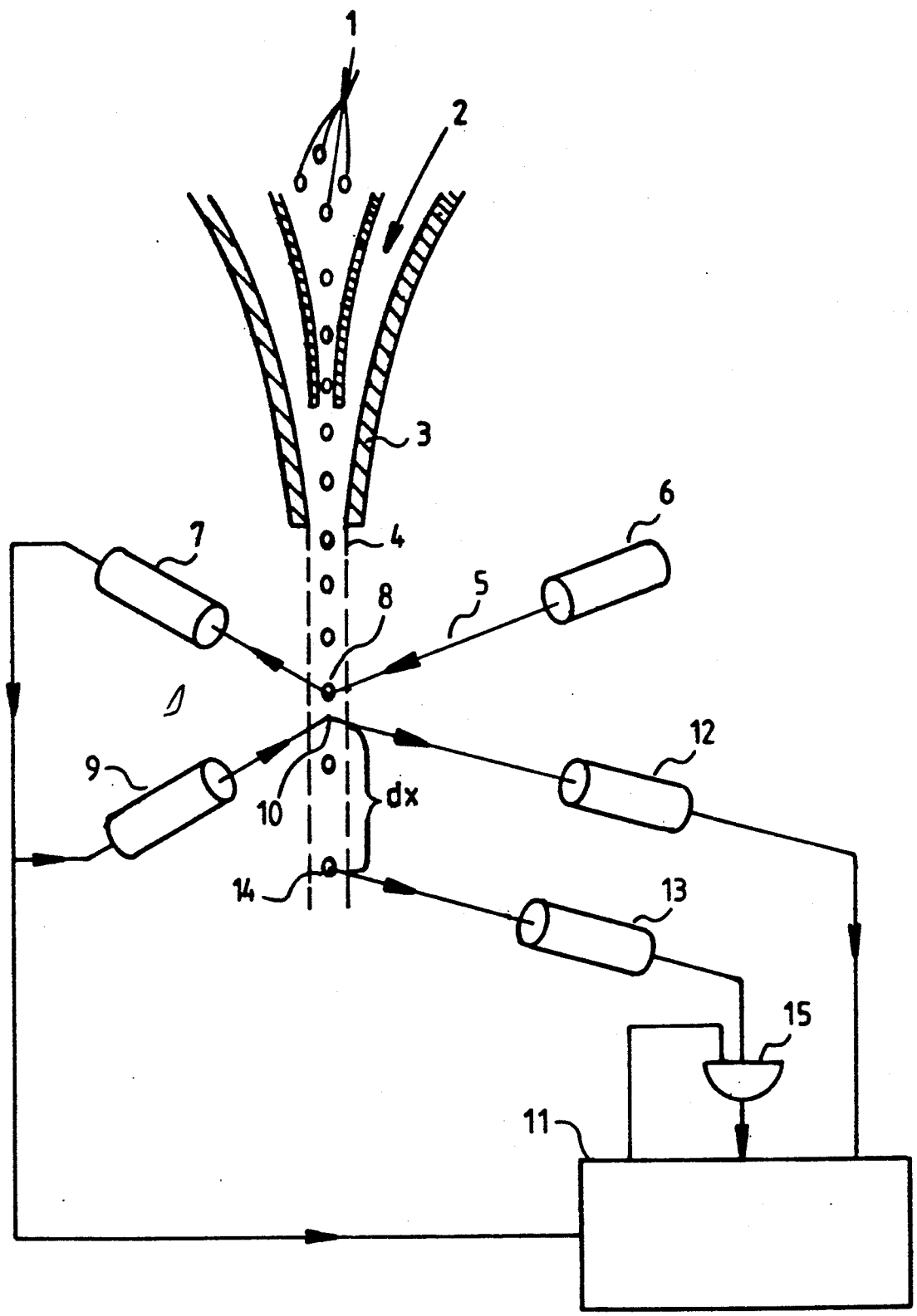

United States Patent [19]

Soini

[11] Patent Number: 5,028,545
[45] Date of Patent: Jul. 2, 1991

[54] BIOSPECIFIC MULTIANALYTE ASSAY METHOD

[75] Inventor: Erkki J. Soini, Turku, Finland

[73] Assignee: Wallac OY, Finland

[21] Appl. No.: 204,258

[22] Filed: Jun. 9, 1988

[30] Foreign Application Priority Data

Jun. 16, 1987 [SE] Sweden ............................ 8702511

[51] Int. Cl.$^5$ .................. G01N 33/566; G01N 33/53; C12Q 1/00; C12Q 1/68
[52] U.S. Cl. ....................................... 436/501; 435/6; 435/7.1
[58] Field of Search .................... 436/501; 435/6, 7

[56] References Cited

U.S. PATENT DOCUMENTS 4,584,277  4/1986  Ullman .

FOREIGN PATENT DOCUMENTS

| 2121262 | 3/1984 | European Pat. Off. . |
| 2121442 | 4/1984 | European Pat. Off. . |
| 2126540 | 11/1984 | European Pat. Off. . |
| 2193356 | 2/1986 | European Pat. Off. . |
| 1219309 | 10/1986 | European Pat. Off. . |
| 2126341 | 8/1983 | United Kingdom . |
| A1/80/02076 | 10/1980 | World Int. Prop. O. . |

OTHER PUBLICATIONS

Saunders, et al., Amplified Flow Cytometric Separation-Free Fluorescence Immunoassays. Clin. Chem. 31/12, 2020-2023 (1985).
Syvänen, et al., Time Resolved Fluorometry: A Sensitive method to quantify DNA hybrids. Nucleic Acid Research, vol. 14, No. 2 (1986) 1017-1028.
Johansen, L., Nustad, K., Orstavik, T., Ugelstad, J., Berge, A., Ellingsen, T., "Excess Antibody Immunoassay for Rat Glandular Kallikrein, Monosized Polymer Particles as the Preferred Solid Phase Material", J. Immunol. Methods (1983) 255-264.
Lightfoote, M., Folks, T. M., Redfield, R., Gold, J., Marti, G. E., Kelly, J., Sell, K. W., "Flow-cytometric Detection of Circulating Immune Complexes", J. Immunol. Methods, 95, (1986) 107-112.
Lisi, P. J., Hueng, C. W., Hoffman, R. A., Teipel, J. W., "A Fluorescence Immunoassay for Soluble Antigens Employing Flow Cytometric Detection", Clin. Chim, Acta 120, (1982) 171-179.
McHugh, T. M., Stites, D. P., Casavant, C. H., Fulwyler, M. J., "Flow Ccytometric Detection and Quantitation of Immune Complexes Using Human Clq Coated Microspheres", J. Immunol. Methods, 95 (1986) 57-61.
Steinkamp, J. A., "Flow Cytometry", Rev. Sci. Instrum. 55(9) Sep. 1984.
Nucleic Acids Research, vol. 14, No. 2, 1986, pp. 1017-1028 (Syvanen A.-CH et al.) "Time Resolved Fluorometry: A Sensitive Method to Quantify DNA-Hybrids".

Primary Examiner—Robert A. Wax
Assistant Examiner—Bradley L. Sisson
Attorney, Agent, or Firm—Fred Philpitt

[57] ABSTRACT

In a biospecific multianalyte assay the use of microspheres and fluorescent labels with substantially different fluorescence decay times, is combined. The assay is performed in a suspension of microspheres in the form of a pool of different microsphere categories, where the categories represent different analytes. The microspheres belonging to the respective categories are first coated with a specific reactant, i.e. the microspheres function as a solid support for the reactant and for a biospecific reaction. Fluorescent labels having a short decay time are used to identify the category of each individual microsphere, while fluorescent labels having a long decay time are used to determine the concentration of a particular analyte on the microsphere by means of the biospecific reaction.

1 Claim, 2 Drawing Sheets

BIOSPECIFIC MULTIANALYTE ASSAY METHOD

The invention relates to a biospecific multianalyte assay method.

Immunoassays are a well established group of biospecific assays and now widely used in routine diagnostics and research laboratories. Another group of biospecific assays, still being developed, is DNA hybridization assays. Biospecific assays generally employ one or several biospecific reactants (e.g. antibody, DNA probe) and normally one of these reactants is labelled. The labels currently used are radioisotopic, enzymatic, luminescent and fluorescent labels.

In routine diagnostics there is a growing need for multianalyte (multiparameter) analysis. Unfortunately, the present methodology does not allow the use of more than two or three simultaneous labels because the spectrometric separation of the signals from different labels is not sufficiently efficient. The emission spectra of different radioisotopic labels and fluorometric labels have a significant overlapping and consequently they provide inadequate separation of different analytes over a required concentration range.

The purpose of this invention is to improve the methodology for biospecific multianalyte assays.

The method according to the invention is characterized by preparing categories of microspheres representing different analytes to be assayed, said categories comprising different amounts of a fluorescent substance having a short decay time, coating each category of microspheres with a biospecific reactant, pooling the different categories of microspheres together in a suspension, adding a sample containing analytes to be assayed to the suspension, adding a mixture of biospecific reactants labelled with a fluorescent compound having a long decay time to the suspension to initiate biospecific reactions between the analytes and the labelled reactants and microsphere-associated reactants, diluting the suspension to reduce the concentration of labelled reactants not bound to the microspheres, exciting both the fluorescent substance having a short decay time and the fluorescent compound having a long decay time, associated with the microspheres, to generate fluorescence emissions, converting the fluorescence emissions to electrical signals, identifying the category of each microsphere on the basis of the strength of the electrical signal resulting from the short decay time fluorescent substance, measuring the concentration of the analyte on each microsphere on the basis of the strength of the electrical signal resulting from the long decay time fluorescent compound.

Figure 2:
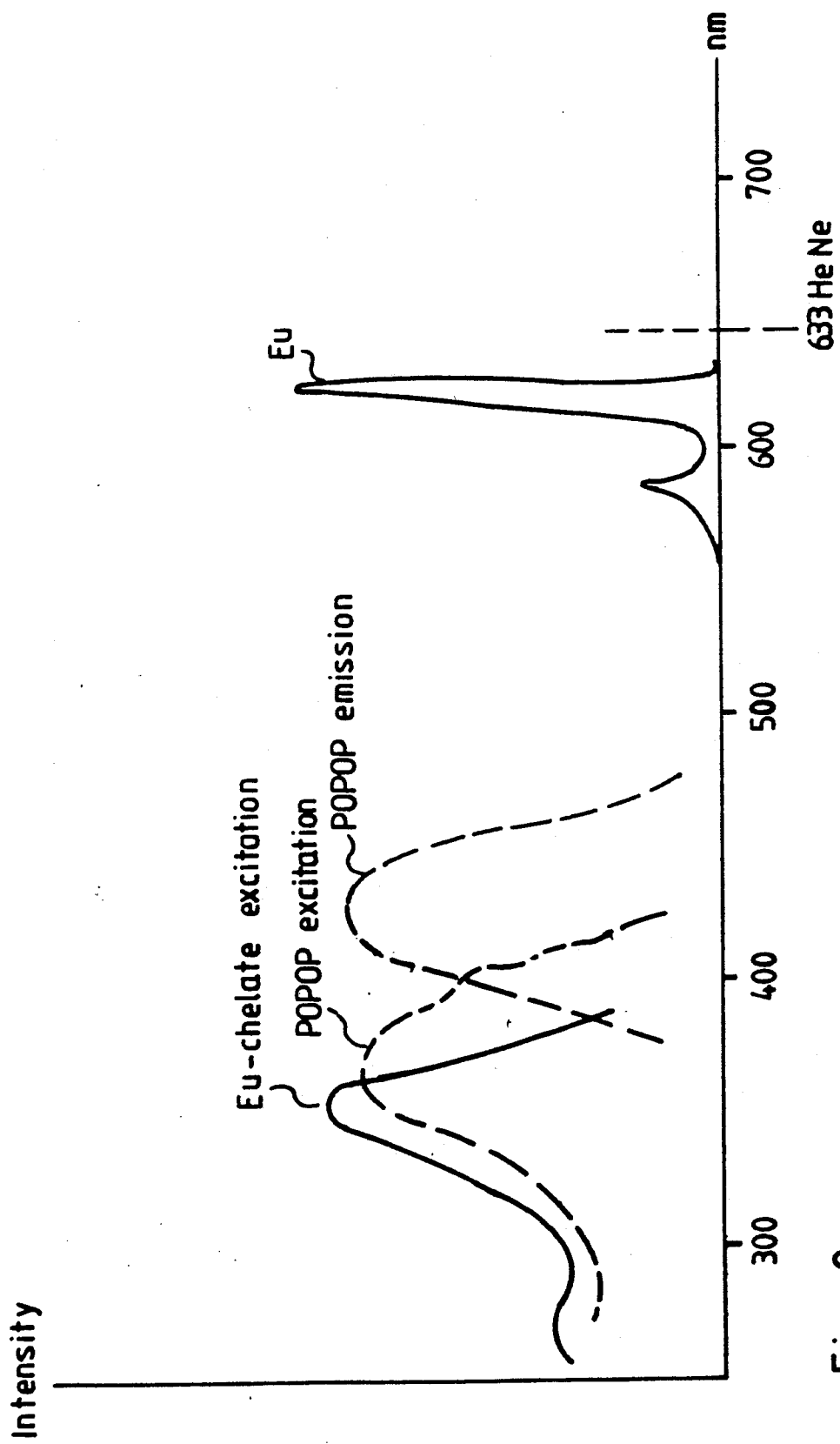

The invention will be described more in detail with reference to the accompanying drawings on which FIG. 1 schematically shows an embodiment of an apparatus for carrying the method according to the invention into effect, and FIG. 2 shows excitation and emission spectra.

The invention combines the use of microspheres and fluorescent labels with substantially different fluorescence decay times. The multianalyte assay is performed in a suspension of artificially manufactured microspheres, comprising a pool of different microspheres representing different analytes, here called categories. Each category of microspheres is first coated with a specific reactant (antibody), i.e. the microspheres function as solid supports for said specific reactant and for the biospecific reaction. This invention is particularly related to a new microfluorometric methodology combining short decay time and long decay time fluorescent labels where short decay time labels are used for identification of the category of each individual microsphere representing different analytes and the long decay time labels are used for detecting the concentration of the particular analyte on the microsphere by means of a biospecific reaction.

Monosized microspheres can be made of appropriate polymer material with slight hydrophilic character and therefore are well suited for water suspensions. The microsphere surface properties allow also binding of macromolecules by physical adsorption as well as by covalent coupling through activation of OH-groups at the surface (L. Johansen & al., Journal of Immunological Methods, 59 (1983) pp. 255-264). In this invention the sample including all different analytes is first incubated with a pool of microspheres and with a pool of labelled reactants in smallest possible volume (for example 10–100 $\mu$l) in order to achieve a complete reaction in a short time. Because of the very small average distance between the analyte molecules and labelled reactants in the microsphere suspension, the equilibrium of the biospecific reaction is achieved rapidly during the incubation and as a result conjugates consisting of the labelled reactant, the analyte and the immobilized reactant on the microsphere surface are formed, commonly called "sandwiches" in the literature. After the incubation the suspension is diluted adequately for analyzing the individual microspheres fluorometrically. A sufficient number of microspheres are analyzed and the fluorescence signals from each microsphere are registered in a computer.

In this invention high detection sensitivity of the fluorescent labels associated with the biospecific reactants at the microparticle surface is based on the use of long decay time fluorescent labels e.g. lanthanide chelates of europium, terbium, etc. as described in more details for example in the European patent application 86850172.7. The detection sensitivity is improved by reducing the background fluorescence with temporal resolution between the excitation and the emission which is usually called time-resolved fluorescence detection in the literature. A comprehensive review of the most recent developments and the evolution of the time-resolved fluorometry of long decay time fluorescent labels has been written by Soini and Lövgren (CRC Critical Reviews in Analytical Chemistry, Vol. 18, Issue 2(1987)). A device for time-resolved fluorescence detection typically incorporates a pulsed light source and a gated detector, which is activated after a certain delay time from the excitation pulse. Thus the short decay time fluorescence or the scattering is not registered by the detector because its lifetime is much shorter than the time delay. The detector detects only long decay time emission which is specific to the long decay time fluorescent label in the sample.

The system relative to this invention combines the features referred to above and the objective of this invention is to identify each individual microparticle representing different analyte categories for the purpose to perform a multianalyte assay in the same sample. The identification is based on detection of short decay time fluorescence as discussed above. In an appropriate measuring system, the short decay time and the long decay time fluorescence can be separately detected. In particular, when the decay times differ several orders of magnitude (organic fluorescent material in the nanosecond range and lanthanide chelates in the microsecond to millisecond range), a strong and variable short decay time fluorescence component makes negligible contribution to the detection of the long decay fluorescence component. This is the crucial point of this invention and the fast decaying fluorescent material can be used for identification of the categories of the microparticles without any significant interference to the determination of the analyte concentration.

Microspheres can be manufactured combining the polymer material with a suitable short decay time fluorescent compound. Organic fluorescent compounds with very short decay time, for example POPOP, bisMSB etc., can be added to any monomer (as discussed e.g. in "Theory and Practice of Scintillation Counting", J. B. Birks, Pergamon Press, 1967, pp. 321-353) and solid fluorescent material is formed in polymerization. The material is processed into microspheres in the same step. For identification of the microspheres, the short decay time organic fluorescent compounds are added into different batches of the monomer in substantially different concentrations differing e.g. by a factor of two from each other.

The identification signal is detected simultaneously with the excitation which lasts for at the most some microseconds and is substantially shorter than the decay time of the long decay time fluorescent label. The contribution of the long decay time fluorescence label to the identification signal level is very low because the photon emission rate of the long decay time component per microsecond is very low and because the identification compound can be used in much higher concentrations than the long decay time label.

The Use of Flow Cytometers as Analysers

It is known that flow cytometers (J. Steinkamp, Rev. Sci. Instrum. 55 (1984) pp. 1375-1400) can be used for immunoassays employing microspheres as a solid support (P. J. Lisi & al., Clinica Chimica Acta, 120 (1982) pp. 171-179). In this method antigen-coated or antibody-coated microspheres (1-50 μm diameter) were allowed to react with the sample and with fluorescent-labelled antigen or antibody in any generally employed immunoassay format, i.e. competitive binding, double antibody "sandwich", etc. The suspension was introduced unwashed into a flow cytometer and the microspheres flowed in a narrow stream past a laser beam. Provided that the cytometer simultaneously measured fluorescent light and scattered light from the microspheres, it was possible to measure only the microsphere-associated fluorescence. Consequently the special advantage of this methodology was that no macroscopic separation of bound and free labelled compounds were needed. Macroscopic separation was circumvented by the ability of the flow cytometer to discriminate, at the microscopic level, particle associated (bound) fluorescence from solution-associated (free) fluorescence. The discrimination was most efficient for 1-5 μm diameter microspheres, where spheres in a highly fluorescent background medium and spheres in a buffer medium displayed approximately the same fluorescent intensity per particle.

A possibility of using flow cytometers for multianalyte immunoassay has been discussed by T. M. McHugh & al., J. Immunol. Methods 95 (1986) pp 57-61 where microspheres of different sizes were used as solid support and the identification of microspheres associated with different analytes was based on analysing the sizes of microspheres. This has been found feasible, because the flow cytometer can accurately detect particles based on size and it would be possible to identify a known microsphere population and to determine the fluorescence without interference from other size microspheres.

In a flow cytometer the concept of temporal resolution between short decay time fluorescence and long decay time fluorescence is, however, not based on the use of the gated detector as described above. The temporal resolution between the excitation and emission can be achieved by high speed movement of the sample in relation to the focal points of excitation and detection. In this concept, as discussed in more details in the Swedish patent application 8604434-4, the focal points of excitation and emission are separated by a small distance in such a way that the signals from scattering and short decay time fluorescence are not detected but the signals from any long decay time fluorescent label can be detected, because of their "after glow" when the sample moves at a high speed in relation to the focal points.

An apparatus incorporating the features discussed above, can be constructed for example as illustrated in FIG. 1. In this example it has been supposed that an europium chelate is used as a long decay time label and POPOP is used as a short decay time fluorescent substance, i.e. identification substance. The excitation wavelengths of europium chelates and POPOP are generally in the same range between 300 nm and 360 nm. The 337 nm wavelength emission from a nitrogen laser or from a xenon flash lamp is optimal for excitation. Emission wavelengths are 613 nm for europium and around 400 nm for POPOP. The excitation and emission spectra are shown in FIG. 2.

A suspension of microparticles 1 and a sheath fluid 2 are moving through a sheath flow nozzle 3 into a thin laminar flow 4, which is first illuminated with a light beam 5 from a continuous light source 6, for example a HeNe-laser at a wavelength of 633 nm, focussed to a point 8 in the laminar flow 4. A photon detector 7 sensitive for 633 nm is focussed to the point 8 and used for monitoring the photon scattering from randomly incoming microparticles 1. Each microparticle 1 produces a signal in the detector 7 and this signal is used for triggering a flash lamp or a pulsed laser 9 which is focussed to a point 10 in the laminar flow 4. The pulsed light source 9 is used for excitation of both fluorescent substances, i.e. the identification compound and the lanthanide chelate in the microparticles at a wavelength of 337 nm. The signal from the detector 7 also activates a computer 11. A gated photon detector 12 sensitive for a wavelength of 400 nm is focussed to the point 10 and measures the amplitude of the short decay time signal from the organic fluorescent compound of each microparticle 1. This amplitude measurement is then used for identification of the particle by the computer 11. A detector 13 measures the long decay time fluorescence at a wavelength of 614 nm. The detector 13 is focussed to a point 14 at a small distance dx downstream from the point 10. The small distance $dx = v \cdot t_d$, where v is the speed of the laminar flow 4 and $t_d$ is a delay time. A gate 15 is activated for a counting time $t_g$ after the delay time $t_d$. The delay time $t_d$ and the counting time $t_g$ are controlled by the computer 11 and are optimized for highest signal-to-background ratio and depend on the decay time of the long decay time fluorescent label. The counting speed of the system depends on the maximum pulse frequency of the pulsed light source 9 and on the counting time $t_g$ of the signal from the long decay time label. Signals from microparticles which coincide within a time interval shorter than the minimum light pulse period, can be electronically rejected. The computer 11 integrates photon signals from microparticles separately for each parameter. Using appropriate standard samples of each analyte, the system can be calibrated for concentration units.

The choice of long decay time fluorescent label affects the system parameters of the device. A special care should be taken for the leakage of stray light from the light source 6 to the detector 13. Good optics for focussing, optical separation of the points 8 and 14 as well as gating the detectors reduce the background caused by this effect.

The Use of Stationary Microfluorometric Analysers

The flow cytometric systems are relatively expensive and their optical and hydrodynamic systems are mechanically complex and sensitive. However, the analysis of the microparticles can also be performed in a stationary state or in a stopped-flow system and this type of approach may be less expensive and more robust. The stationary instrumental approach is based on the use of microscopic observations of microparticles in a thin cavity into which the diluted microparticle suspension is pumped from a reaction tube. The suspension of the microparticles is first scanned at a very rapid rate and the identification of the microspheres as well as their location and determination of their analyte categories take place on the basis of the detection of short decay time fluorescence. The detection of the analyte concentration in the microparticles takes place measuring the signal strength of long decay time fluorescence. A sufficient number of randomly located microparticles are identified and analyzed in order to obtain a sufficient amount of information for desired statistical precision.

The excitation light source can be either a pulsed light source or a constant light source. If using a pulsed light source, each scanned point of the sample is exposed to one or several light pulses and the detector and the associated photon counting electronics is gated for detection of both short decay time and long decay time fluorescence separately.

If the constant light source is used in a confocal scanning microfluorometry, the concept of temporal resolution between short decay time fluorescence and long decay time fluorescence can be achieved in the following manner. The focal points of the excitation and the emission are separated by a small distance in such a way that the signals from the short decay time fluorescence and the signals from the long decay time fluorescent label can be detected at different times when the excitation beam moves at a high speed in relation to the sample. This concept is discussed in more detail in the Swedish patent application 8604434-4.

Microfluorometric analysis (as well as flow cytometric) can discriminate between the microsphere-associated fluorescence and solution-associated fluorescence, because the respective concentrations in the microscopic focal point in the diluted suspension differ many orders of magnitude. This detection concept provides a reasonable separation of the free and the bound fractions but if necessary, it can be made more efficient using normal separation methods (washing, filtration, centrifugation etc.)

Detection of various fluorescence signals can be made with an appropriate computer controlled automatic video microscope (Video Microscopy, ed. Shinya Inoue, Plenum Press, 1986) or with a scanning microscope. The scanning microscope can also be equipped with confocal optical systems for excitation and emission in order to improve sensitivity and precision. (G. J. Brakenhof & al., J. Microscopy, 117 (1979) pp. 219-232). Alternatively the aperture can be selected optimally according to the diameter of the microparticles and scanning of the fluorescence emission signals can be made using an appropriate imaging detector which can work in a single photon mode. Such detectors can be composed for example of microchannel plate image intensifiers and charge coupled imaging devices (CCD). Charge coupled devices can be gated for the purpose of time resolved operation in order to discriminate between short decay time fluorescence and long decay time fluorescence (see Video Microscopy, ed Shinya Inoue). Analysis of the image from the CCD can be performed with a computer.

I claim:

1. Biospecific multianalyte assay method, characterized by preparing categories of microspheres representing different analytes to be assayed, said categories comprising different amounts of a fluorescent substance having a short decay time, coating each category of microspheres with a biospecific reactant, pooling the different categories of microspheres together in a suspension, adding a sample containing analytes to be assayed to the suspension, adding a mixture of biospecific reactants labelled with a fluorescent compound having a long decay time to the suspension to initiate biospecific reactions between the analytes and the belled reactants and microsphere-associated reactants, diluting the suspension to reduce the concentration of labelled reactants not bound to the microspheres, exciting both the fluorescent substance having a short decay time and the fluorescent compound having a long decay time, associated with the microspheres, to generate fluorescence emissions, converting the fluorescence emissions to electrical signals, identifying the category of each microsphere on the basis of the strength of the electrical signal resulting from the short decay time fluorescent substance, measuring the concentration of the analyte on each microsphere on the basis of the strength of the electrical signal resulting from the long decay time fluorescent compound.

* * * * *